US00PP27246P2

(12) United States Plant Patent
Kordes

(10) Patent No.: US PP27,246 P2
(45) Date of Patent: Oct. 11, 2016

(54) MINIATURE ROSE PLANT NAMED 'KORPOT055'

(50) Latin Name: *Rosa hybrida*
Varietal Denomination: KORpot055

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes' Sohne Rosenschulen GmbH & Co. KG, Offenseth-Sparrieshoop (DE)

( * ) Notice: Subject to any disclaimer, the term of this patent is extended or adjusted under 35 U.S.C. 154(b) by 109 days.

(21) Appl. No.: 14/544,530

(22) Filed: Jan. 14, 2015

(51) Int. Cl.
*A01H 5/02* (2006.01)

(52) U.S. Cl.
USPC ..... Plt./118

(58) Field of Classification Search
USPC ..... Plt./116, 118
See application file for complete search history.

*Primary Examiner* — Susan McCormick Ewoldt

(57) ABSTRACT

A new and distinct variety of rose with long lasting, novel yellow flowers, and attractive foliage with above average disease resistance. It exhibits compact to upright growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORpot055'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 2011. The crossing was between an un-named seedling, the seed parent, and another un-named seedling, the pollen parent by the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORpot055'.

SUMMARY OF THE INVENTION

The new rose plant may be distinguished from its seed parent, an un-named seedling, by the following combination of characteristics:

1. 'KORpot055' has yellow petals, whereas the un-named seedling has yellow petals with red edges.
2. 'KORpot055' has longer shelf-life than the un-named seedling.

The new rose plant may be distinguished from its pollen parent, an un-named seedling, by the following combination of characteristics:

1. 'KORpot055' has yellow flowers, whereas the un-named seedling has cream-colored flowers.
2. 'KORpot055' has a very double petal count, whereas the un-named seedling has a semi-double petal count.

The objective of the hybridization was to create a new and distinct rose plant with unique qualities, such as:

1. Compact and uniform growth and flowering under greenhouse conditions when grown as a potted floral plant;
2. Abundant, long lasting, and attractive flowers and foliage;
3. Resistance to diseases encountered in greenhouse and nursery culture; and
4. Suitability for production from softwood cuttings in floral and nursery containers.

This combination of qualities is not present in prior rose cultivars known to the inventor. These objectives have been substantially achieved and in that distinguish 'KORpot055' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORpot055' was selected in April 2012 from the seedling beds to be asexually propagated for further evaluation. The first asexual propagation of 'KORpot055' was done by rooting softwood cuttings in June 2012 at the inventor's nursery in Offenseth-Sparrieshoop, Germany.

These initial and other subsequent propagations conducted in controlled environments demonstrate that 'KORpot055' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORpot055'.

DETAILED BOTANICAL DESCRIPTION

The following is a description of 'KORpot055', as observed growing in December 2014 in a nursery in Jackson County, Oreg. on plants of 8 months of age. Color references are made using The Royal Horticultural Society (London, England) Colour Chart, 2001 except where common terms of color are used.

For a comparison, several physical characteristics of the rose variety 'KORfrosdra', a rose variety from the same inventor described and illustrated in U.S. Plant Pat. No. 20,208 and issued on Aug. 4, 2009 are compared to 'KORpot055' in Chart 1.

CHART 1

| Characteristic | 'KORpot055' | 'KORfrosdra' |
|---|---|---|
| Petal Count. | Average of 70 petals under normal growing conditions. | Approximately 25-30 petals under normal growing conditions. |
| Bud Size Upon Opening. | 65 mm in length from the base of receptacle to distal end of bud and 15 mm in diameter at its widest point. | 35 mm in length from base of receptacle to end of bud and 18 mm in diameter at its widest point. |
| Growth Habit. | Compact to upright. When grown as a 15 cm pot plant, the average height of the plant is 35 to 50 cm. | Compact to bushy. When grown as a 15 cm pot plant, the average height of the plant is 26 to 28 cm. |

Parents:

*Seed parent*.—An un-named seedling.

*Pollen parent*.—An un-named seedling.

Classification:

*Botanical classification*.—*Rosa hybrida* 'KORpot055'.

*Commercial classification*.—Miniature rose.

FLOWER AND FLOWER BUD

Blooming habit: Recurrent. Floriferous.

Flower bud:

*Size*.—Upon opening, 65 mm in length from base of receptacle to distal end of bud and 15 mm diameter at its widest point.

*Bud form*.—Very long. Pointed ovoid.

*Bud color*.—As sepals first unfold, bud color is Yellow Group 10A. Intonations of Yellow-Green Group 145A on midrib. When ¼ open, the upper surface of petals is Yellow Group 13B, and the lower surface is Yellow Group 11A.

*Sepals*.—Color: Upper surface: Yellow-Green Group 146B. Intonations of Yellow-Green Group 146D at base and along midrib. Lower surface: Yellow-Green Group 146B Anthocyanin: Greyed-Purple 183B. Location: At apices and on stipitate glands. Size: Average 45 to 50 mm (l)×6 to 7 mm (w). Calyx Diameter: 75 to 100 mm. Shape: Weak foliaceous appendages on 2 to 3 of the five sepals. Apex: Apiculate. Base: Flat at union with receptacle. Quantity: Five. Surface texture: Upper side: Hoary. Lower surface: Papillate. Margins: Cilliate and glandular toothed margins observed. Stipitate glands: Abundant on lower service, limited numbers on margins.

Flower bloom:

*Fragrance*.—Light.

*Duration*.—On the plant 15 to 18 days. Senesced petals drop away cleanly.

*Size*.—Medium for a miniature rose. When open, the average flower diameter is 45 to 50 mm and the average flower height is 35 to 40 mm.

*Form*.—Shape: Round. Rosette. Shape of flower when viewed from the side: Upon opening, upper part: Flat. Upon opening, lower part: Flat. Open flower, upper part: Flat. Open flower, lower part: Flattened convex.

Color:

*Upon opening, petals*.—Outermost petals: Outer Side: Yellow Group 12B. Inner Side: Yellow Group 9A. Innermost petals: Outer Side: Yellow Group 12A. Inner Side: Yellow Group 12A.

*Upon opening, basal petal spots*.—No distinctive coloration at petal base observed.

*After opening, petals*.—Outermost petals: Outer Side: Yellow Group 8A. Inner Side: Yellow Group 8A. Innermost petals: Outer Side: Yellow Group 12A. Inner Side: Yellow Group 12A.

*After opening, basal petal spots*.—No distinctive coloration at petal base observed.

General tonality: On open flower Yellow Group 13B. No change in the general tonality at the end, of the 8th day. Afterwards, general tonality is Yellow Group 13D.

Petals:

*Petal count*.—Very Double. Approximately 70 petals under normal conditions.

*Petal reflex*.—Petals reflex very slightly. Reflex occurs one by one.

*Petal margin*.—Entire. Ruffled edges observed on some innermost petals.

*Petal shape*.—Outermost Petals: Orbicular. Apex: Mucronate. Base: Obtuse. Innermost Petals: Obovate. Apex: Mucronate. Base: Cuneate.

*Petal size*.—15 to 40 mm (l)×10 to 40 mm (w).

*Petal arrangement*.—Not formal.

*Texture*.—Inner Side: Smooth. Outer Side: Smooth.

Petaloids:

*Petaloid count*.—Average of 5 per flower.

*Petaloid size*.—8 to 15 mm (l)×3 to 8 mm (w).

*Petaloid color*.—Inner side: Yellow-Orange Group 14A. Outer side: Yellow-Orange Group 14A.

*Petaloid texture*.—Inner Side: Smooth. Outer Side: Smooth.

*Margins*.—Undulated.

*Petaloid shape*.—Most commonly oblanceolate, with some petaloids highly irregular. Apex: Acute. Base: Attenuate.

Reproductive organs:

*Pistils*.—Average. Approximately 60 present. Stigmas: Location: Slightly inferior to equal in position to anthers. Color: Yellow Group 8A. Diameter: 0.5 to 1 mm. Styles: Length: About 5 to 6 mm long. Color: Yellow Group 2D.

*Stamens*.—Approximately 100 on average and regularly arranged. Anthers: Size: Average 1.5 to 2 mm (l)×1 to 1.5 mm (w). Pollen: Generally present. Color: Greyed-Orange Group 163B. Filaments: Color: Yellow-Orange Group 15A. Length: 5 to 8 mm.

Receptacle:
*Surface*.—Glossy, without hairs or stipitate glands.
*Color*.—Yellow-Green Group 144A.
*Shape*.—Pear-shaped.
*Texture*.—Glabrous.
*Size*.—8 to 10 mm (h)×7 to 9 mm (w).

Pedicel:
*Surface*.—Limited to moderate numbers of fine hairs and abundant stipitate glands.
*Length*.—60 to 110 mm average length.
*Diameter*.—2 to 3 mm average diameter.
*Color*.—Yellow Green Group 144A.
*Intonations*.—Greyed-Purple 185C. Locations: On stipitate glands.
*Strength*.—Somewhat strong.
*Texture*.—Papillate.

Peduncle:
*Surface*.—With fine hairs and stipitate glands.
*Length*.—55 to 75 mm average length.
*Diameter*.—2.5 to 3.5 mm average diameter.
*Color*.—Yellow-Green Group 144A.
*Intonations*.—Greyed-Purple Group 185C on stiptiates.
*Strength*.—Moderately strong.
*Borne*.—Typically singularly. Occasionally multiple flower buds per inflorescence, generally 2 to 3. Below initiation of inflorescence, flowering laterals are generally present.

THE PLANT

Growth: Moderately vigorous.

Plant habit: Compact to upright. When grown as a 15 cm pot plant, the average plant height is 35 to 50 cm and the average plant width is 20 to 30 cm.

Stems:
*Stem color*.—Young wood: Yellow-Green Group 144A. Older wood: Yellow-Green Group 144A.
*Intonations*.—Greyed-Purple Group 184B. Primarily present on young wood.
*Stem surface texture*.—Young wood: Smooth. Older wood: Smooth.
*Length*.—25 to 45 mm average length when grown under commercial greenhouse floral production.
*Diameter*.—3 to 4 mm average diameter.

Prickles: Present.
*Incidence*.—Average of 5 to 7 per each 10 cm of stem.
*Size*.—Average length: 4 to 6 mm.
*Color*.—Immature prickles: Yellow-Green Group 145C. Mature prickles: Yellow-Green Group 145C.
*Shape*.—Linear.
*Anthocyanin*.—Greyed-Purple 184C.

Leaves: Normally 5 leaflets on normal leaves in middle of the stem.
*Venation pattern*.—Pyramidal net pattern.
*Leaf size*.—120 to 150 mm (l)×90 to 125 mm (w).
*Abundance*.—Average.

Leaflets:
*Size*.—Average size of the terminal leaflet is 65 to 75 mm (l)×30 to 40 mm (w).
*Shape*.—Ovate. Base: Obtuse. Apex: Acuminate.
*Margins*.—Serrated.
*Surface*.—Upper surface: Glossy. Lower surface: Semi-glossy.
*Texture*.—Upper side of leaflet: Leathery. Under side of leaflet: Leathery.
*Color, mature foliage*.—Upper Leaflet Surface: Green Group 139A. Lower Leaflet Surface: Yellow-Green Group 148B.
*Color, juvenile foliage*.—Upper Leaflet Surface: Yellow-Green Group 146A. Lower Leaflet Surface: Yellow-Green Group 146B.
*Anthocyanin intonation*.—Greyed-Purple 184B. Location: Margins and occasionally undersides of mature foliage. Covers most immature foliage.
*Arrangement*.—Odd pinnate.
*Venation*.—Reticulate.

Stipules:
*Size*.—20 to 30 mm (l)×3 to 5 mm (w).
*Stipule color*.—Yellow-Green Group 146B.
*Anthocyanin*.—Greyed-Purple 185B present on stipitate glands.
*Stipitate glands*.—Abundant on margins.
*Margins*.—Glandular toothed.
*Texture*.—Glabrous.
*Shape*.—Apex: Apiculate. Base: Winged.

Petiole:
*Length*.—Average 25 to 40 mm.
*Diameter*.—Average 1 to 1.5 mm.
*Petiole color*.—Upper surface: Yellow-Green Group 146B. Underneath: Yellow-Green Group 146C.
*Margins*.—Glandular toothed.
*Anthocyanin*.—Greyed-Purple 185A present on margins.
*Prickles*.—One to two small prickles present underneath.
*Stipitate glands*.—Abundant on margins.
*Texture*.—Upper surface: Papillate. Underneath: Glabrous.

Petiole rachis:
*Length*.—Average 15 to 25 mm.
*Diameter*.—Average 1 mm.
*Color*.—Yellow-Green 146B.
*Anthocyanin*.—Greyed-Purple 185A present on margins.
*Margins*.—Glandular toothed.
*Prickles*.—A few small prickles underneath.
*Stipitate glands*.—Limited numbers of stipitate glands on margins.

Hips/seed formation: None observed.

Winter hardiness: Due to the variety's principle use in greenhouses, winter hardiness has not been evaluated.

Disease resistance: Above average resistance to Powdery mildew (*Sphaerotheca pannosa*) and Botrytis (*Botrytis cinerea*) diseases under normal growing conditions in Jackson County, Oreg.

I claim:

1. A new and distinct variety of rose plant, as described and illustrated herein.

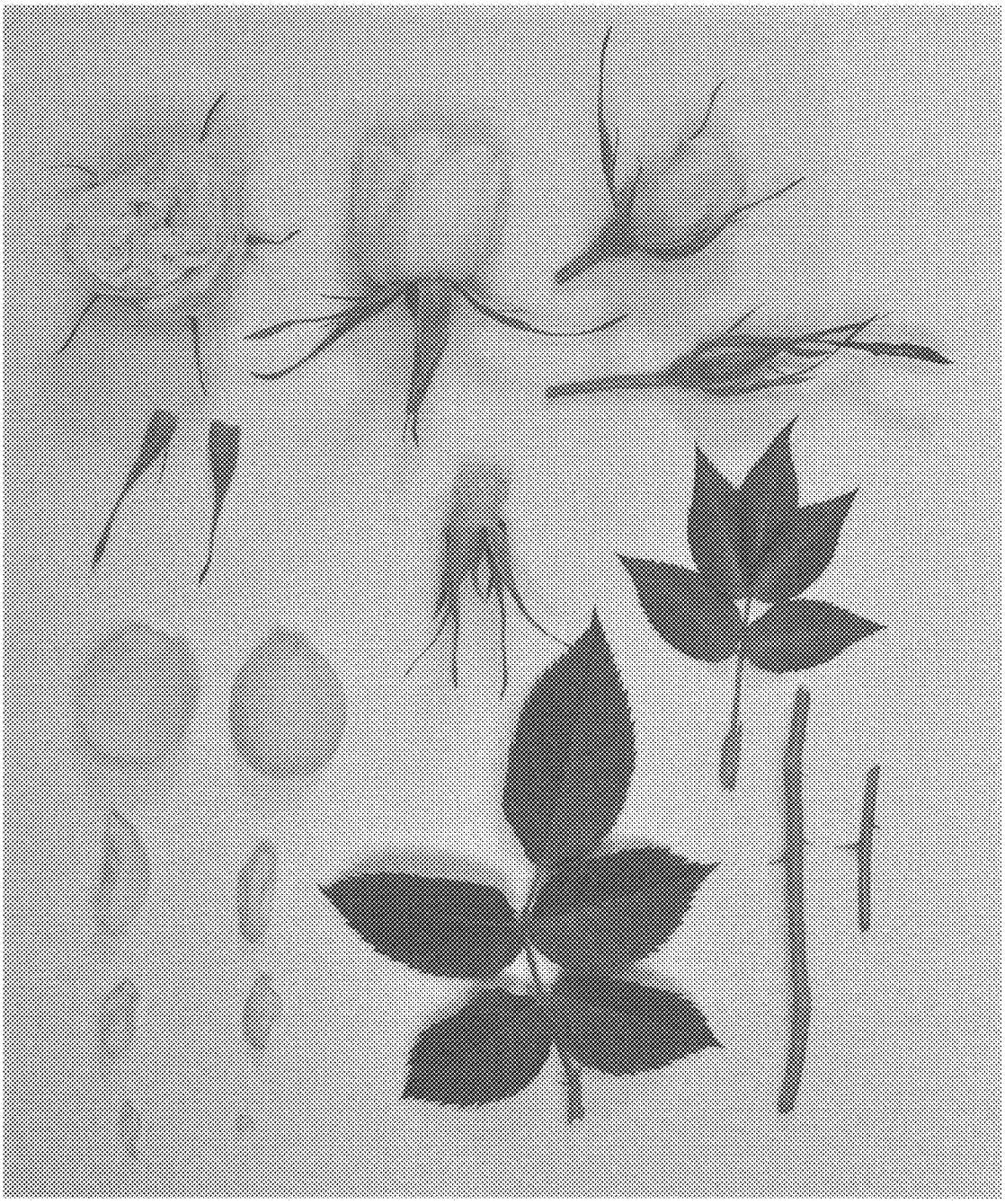

* * * * *